United States Patent [19]

Vogt et al.

[11] 4,018,815

[45] Apr. 19, 1977

[54] PROCESS FOR THE PREPARATION OF POLYESTER POLYOLS

[75] Inventors: Herwart C. Vogt, Grosse Ile; John T. Patton, Jr., Wyandotte, both of Mich.

[73] Assignee: BASF Wyandotte Corporation, Wyandotte, Mich.

[22] Filed: Sept. 29, 1975

[21] Appl. No.: 617,308

[52] U.S. Cl. .................. 260/485 G; 260/75 M; 260/468 K; 260/475 P

[51] Int. Cl.² .................. C07C 69/34; C07C 69/52

[58] Field of Search ........ 260/475 P, 75 M, 485 G, 260/468 K

[56] References Cited

UNITED STATES PATENTS

| | | | |
|---|---|---|---|
| 3,803,210 | 4/1974 | Rod et al. | 260/75 M X |
| 3,907,863 | 9/1975 | Voss | 260/475 P X |
| 3,911,048 | 10/1975 | Vargiu et al. | 260/75 M X |

*Primary Examiner*—Lucille M. Phynes
*Attorney, Agent, or Firm*—Joseph D. Michaels; Bernhard R. Swick; Robert E. Dunn

[57] ABSTRACT

Polyester polyols are prepared by the reaction of a polycarboxylic acid or anhydride with a polyhydric alcohol employing in an initial step a stoichiometric excess of polycarboxylic acid or anhydride, thereafter removing between 90 to 95% of the water of esterification, adjusting the stoichiometry of the reaction by addition of polyhydric alcohol, and continuing the esterification reaction until a polyester polyol having an acid number of less than two is obtained. The process allows for an increase in reactor capacity without equipment modification at the same cycle times and a decrease in side product formation.

6 Claims, No Drawings

PROCESS FOR THE PREPARATION OF POLYESTER POLYOLS

BACKGROUND OF THE INVENTION

1. Field of the Invention

The present invention relates to an improved process for the preparation of polyester polyols. More particularly, the invention relates to an improved multistep batch process for the prepartion of polyester polyols by the reaction of a polycarboxylic acid or anhydride with a polyhydric alcohol.

2. Prior Art

The preparation of polyester polyols by the reaction of a polycarboxylic acid or anhydride with a polyhydric alcohol is well known in the art as evidenced by U.S. Pats. Nos. 3,162,616 and 3,716,523. Generally, the processes of the prior art involve a one-step reaction of a polycarboxylic acid or anhydride with a stoichiometric excess amount of a polyhydric alcohol. An excess amount of alcohol is employed to assure that both ends of the polyester terminate in hydroxyl groups, thus providing polyester polyols of low acid numbers, that is, two or less.

One of the problems associated with the prior art processes of preparing polyester polyols from polycarboxylic acids or anhydrides and polyhydric alcohols is the water formed during the esterification, which must be removed from the reaction site. Since for each mole of polycarboxylic acid or anhydride employed in the preparation of the polyol there is produced from 1 to 2 moles of water, the water occupies valuable reactor space, limiting the amounts of reactants which may be initially charged to the reactor. In the normal accepted procedures for the preparation of polyester polyols, all the reactants are charged to a reactor and as the reaction proceeds the water of esterification is removed from the reactor by distillation. Depending on the polyol and the acid or anhydride employed, the amount of water which is removed is approximately 20 to 30% by weight of the total charge. Thus, the final yield of polyol is generally 20 to 30% less than the weight of the charge. The present invention is directed to an improvement in the above-described prior art processes of preparing polyester polyols which allows for an increase in reactor capacity without equipment modification at the same cycle times.

SUMMARY OF THE INVENTION

The present invention relates to an improved process for the preparation of polyester polyols by the esterification of a polycarboxylic acid or anhydride with a polyhydric alcohol which involves initially heating a stoichiometric excess amount of a polycarboxylic acid or anhydride with a polyhydric alcohol, removing between 90 to 95% by weight of the water of esterification, adjusting the stoichiometry of the reaction by addition of polyhydric alcohol, and continuing the esterification reaction until a polyol having a desired acid number and hydroxyl number is obtained.

DESCRIPTION OF THE PREFERRED EMBODIMENTS

The present invention relates to a process for the preparation of a polyol by the esterification of a polycarboxylic acid or anhydride with a polyhydric alcohol which comprises:

a. initially charging to a reactor an amount of a polycarboxylic acid or anhydride equal to between 3 to 16, preferably 6 to 12, weight percent in excess of stoichiometry;

b. adding to the reactor a polyhydric alcohol and heating the charge to a temperature between 130° to 240° C.;

c. removing from the reactor between 90 to 95 weight percent of the water of esterification resulting from step (b);

d. charging to the reactor an amount of polyhydric alcohol substantially equivalent in weight to the amount of water of esterification removed from step (c); and e. continuing the esterification reaction until a polyol having an acid number of less than two is obtained.

There are two essential reactants employed in the process of the subject invention, namely, a polycarboxylic acid or anhydride and a polyhydric alcohol. Representative polycarboxylic acids and anhydrides which may be employed include oxalic, malonic, succinic, glutaric, adipic, pimelic, suberic, azelaic, sebacic, brassylic, thapsic, maleic, fumaric, glutaconic, $\alpha$-hydromuconic, $\beta$-hydromuconic, $\alpha$-butyl-$\alpha$-ethyl-glutaric, $\alpha$-$\beta$-diethylsuccinic, isophthalic, terephthalic, hemimellitic, and 1,4-cyclohexanedicarboxylic. Any suitable polyhydric alcohol including both aliphatic and aromatic may be used such as ethylene glycol, diethylene glycol, dipropylene glycol, triethylene glycol, tetraethylene glycol, trimethylene glycol, 1,2-propylene glycol, 1,4-tetramethylene glycol, 1,2-butylene glycol, 1,4-butane diol, 1,3-butane diol, 1,5-pentane diol, 1,4-pentane diol, 1,3-pentane diol, 1,6-hexane diol, 1,7-heptane diol, glycerol, 1,1,1-trimethylolpropane, 1,1,1-trimethylolethane, hexane-1,2,6-triol, neopentylglycol, dibromoneopentylglycol, 1,10-decanediol, and 2,2-bis(4-hydroxycyclohexyl)propane.

The esterification reaction of the present invention is generally carried out in the presence of an inert atmosphere such as nitrogen or carbon dioxide. Generally the acid and/or anhydride component and a portion of the polyhydric alcohol are charged to a reactor and with stirring the charge is heated to a temperature between 130° and 240° C. Heating is continued such that the water of esterification can be rapidly removed, generally by distillation. Upon removing between 90 to 95 weight percent of the theoretical water of esterification from the reactor, an additional amount of polyhydric alcohol is charged to the reactor and esterification is continued until the acid number of the polyol is less than two and all of the water of esterification is removed.

Although the reaction proceeds promptly with heating and no catalyst is required, if desired a catalyst may be employed during the reaction, preferably being charged along with or shortly after the second polyhydric alcohol charge. Representative esterification catalysts include organic metal compounds such as those described in U.S. Pat. Nos. 3,162,616 and 3,716,523.

The total time for the esterification reaction may vary from 6 hours to 48 hours, preferably from 12 hours to 24 hours. The time will depend on the reactivity of the reactants, the stoichiometry, temperature, and pressure employed in the reaction, the molecular weight of the resulting polyester polyols, the rapidity with which the water of esterification is removed, and the activity of the catalyst employed, if any.

The polyester polyols prepared in the subject invention are particularly useful in the preparation of polyurethane compositions such as textile coatings (tie coatings and top coatings), elastomers, shoe sole composites, flexible, rigid and microcellular foams, as well as urethane rubbers, sealants, and adhesives.

The following examples illustrate the invention. All parts are by weight unless otherwise indicated.

EXAMPLE I

A reaction vessel equipped with a condenser, agitator, thermometer, column, nitrogen source and inlet and outlet tubes was charged with 1,000 parts (6.84 moles) of adipic acid and 606 parts (5.71 moles) of diethylene glycol. The above charges represent a 11.9 weight percent stoichiometric excess of adipic acid. The vessel was sealed and vacuum purged. The vacuum was then released with nitrogen and the charge was heated to about 140° C. at which temperature water began to distill out of the reactor. Heating continued until the temperature of the charge reached 200° C. during which time water was continually distilled. When approximately 95% by weight (193 parts) of the theoretical amount of water had been removed, 190.4 parts (1.79 moles) of diethylene glycol was charged to the reactor. The total glycol charge was 1% in excess of the stoichiometric amount calculated to yield a polyester diol having a molecular weight of 2440. Heating was continued at a charge temperature of about 225° C. and a pressure of 10 mm. of mercury and water was removed intermittently during this period.

When the acid number of the product reached sixteen, 0.10 part of a tetraalkyltitanate-stannous alcoholate esterification catalyst was added to the reactor and heating continued and water removed until an acid number of less than one was reached. The reactants were then cooled to 100° C. and discharged therefrom. Total cycle or reaction time was 14 hours. The resulting polyester polyol (1467 parts) had a hydroxyl number of 46 and an acid number of 0.6.

The above run was repeated except that 892 parts of adipic acid and 714 parts of diethylene glycol are all charged to the reactor, filling the reactor to capacity. The reaction was then carried out under essentially the same conditions of pressure, temperature, and time. A yield of 1311 parts of polyester polyol having a hydroxyl number of 46 and an acid number of 0.6 was obtained. The amount of polyol represents a 11.9% decrease in yield over the process of the subject invention.

EXAMPLE II

Following the procedure described in Example I with the exception that an esterification catalyst was not employed, a 2000 molecular weight polyester polyol was prepared from adipic acid, ethylene glycol, and 1,4-butane diol. The amounts of reactants employed were as follows:

| Initial Charge: | Parts | Moles |
|---|---|---|
| Adipic Acid | 1143 | 7.82 |
| Ethylene Glycol | 271 | 4.37 |
| 1,4-Butane Diol | 191 | 2.12 |
| Second Charge: | Parts | Moles |
| 1,4-Butane Diol | 195 | 2.16 |

The initial charge represented a 12.2 weight percent excess of adipic acid. The second charge was added after 219 parts of water (95% of theory) had been removed from the reactor. The total glycol charged was 1% in excess of the stoichiometric amount calculated to yield a polyester diol having a molecular weight of 2000. The temperature of the reaction varied from 180° to 225° C. and the pressure was 10 mm. of mercury. The cycle time was 16 hours. The resulting polyester polyol (1437 parts) had a hydroxyl number of 56 and an acid number of 0.5.

The above run was repeated except that 1018 parts of adipic acid, 243 parts of ethylene glycol and 344 parts of 1,4-butane diol are all charged to the reactor at once, filling the reactor to capacity. The total glycol charged was 1% in excess of the stoichiometric amount calculated to yield a polyester diol having a molecular weight of 2000. The reaction was then carried out under essentially the same conditions of pressure, temperature, and time. A yield of 1281 parts of polyester polyol having a hydroxyl number of 56 and an acid number of 0.5 was obtained. The amount of polyol represents a 12.2% decrease in yield over the process of the subject invention.

EXAMPLE III

Following the procedure described in Example I with the exception that an esterification catalyst was not employed, a 1000 molecular weight polyester polyol was prepared from adipic acid and ethylene glycol. The amounts of reactants employed were as follows:

| Initial Charge: | Parts | Moles |
|---|---|---|
| Adipic Acid | 1122 | 7.68 |
| Ethylene Glycol | 384 | 6.19 |
| Second Charge: | | |
| Ethylene Glycol | 186 | 3.00 |

The initial charge represented a 12.5 weight percent excess of adipic acid. The second charge was added after 208 parts of water (95% of theory) had been removed from the reactor. The total glycol charged was 1% in excess of the stoichiometric amount calculated to yield a polyester diol having a molecular weight of 1000. The temperature of the reaction varied from 180° to 235° C. and the pressure was 10 mm. of mercury. The cycle time was 17 hours. The resulting polyester polyol (1340 parts) had a hydroxyl number of 112 and acid number of 0.06.

The above run was repeated except that 998 parts of adipic acid and 508 parts of ethylene glycol are all charged to the reactor at once, filling the reactor to capacity. The total glycol charged was 1% in excess of the stoichiometric amount calculated to yield a polyester diol having a molecular weight of 1000. The reaction was then carried out under essentially the same conditions of pressure, temperature and time. A yield of 1191 parts of polyester polyol having a hydroxyl number of 112 and an acid number of 0.1 was obtained. The amount of polyol represents a 12.5% decrease in yield over the process of the subject invention.

EXAMPLE IV

Following the procedure described in Example I with the exception that an esterification catalyst was not employed, a 2000 molecular weight polyester polyol was prepared from adipic acid and ethylene glycol. The amounts of reactants employed were as follows:

| Initial Charge: | Parts | Moles |
|---|---|---|
| Adipic Acid | 1153 | 7.89 |
| Ethylene Glycol | 352 | 5.67 |
| Second Charge: | | |
| Ethylene Glycol | 187 | 3.01 |

The initial charge represented a 12.5 weight percent excess of adipic acid. The second charge was added after 191 parts of water (95% of theory) had been removed from the reactor. The total glycol charge was 1% in excess of the stoichiometric amount calculated to yield a polyester diol having a molecular weight of 2000. The temperature of the reaction varied from 135° to 225° C. and the pressure was 10 mm. of mercury. The cycle time was 16.18 hours. The resulting polyester polyol (1333 parts) had a hydroxyl number of 56 and acid number of 0.5.

The above run was repeated except that 1026 parts of adipic acid and 480 parts of ethylene glycol are all charged to the reactor at once, filling the reactor to capacity. The total glycol charge was 1% in excess of the stoichiometric amount calculated to yield a polyester diol having a molecular weight of 2000. The reaction was then carried out under essentially the same conditions of pressure, temperature, and time. A yield of 1185 parts of polyester polyol having a hydroxyl number of 56 and an acid number of 0.5 was obtained. The amount of polyol represents a 12.5% decrease in yield over the process of the subject invention.

EXAMPLE V

Following the procedure described in Example I with the exception that the esterification catalyst employed was stannous octoate, a 476 molecular weight polyester polyol was prepared from phthalic anhydride, trimethylolpropane, and tetraethylene glycol. The amounts of reactants employed were as follows:

| Initial Charge: | Parts | Moles |
|---|---|---|
| Tetraethylene Glycol | 7045 | 36.3 |
| Trimethylolpropane | 4278 | 31.9 |
| Phthalic Anhydride | 5377 | 36.3 |
| Second Charge: | | |
| Trimethylolpropane | 592 | 4.4 |

The initial charge represented a 3.6 weight percent excess of phthalic anhydride. The second charge was added after 620 parts of water (95% of theory) had been removed from the reactor. The temperature of the reaction varied from 170° to 210° C. The cycle time was 20 hours. The resulting polyester polyol (15,806 parts) had a hydroxyl number of 357 and acid number of 1.7.

The above run was repeated except that 6800 parts of tetraethylene glycol, 4700 parts of trimethylolpropane and 5190 parts of phthalic anhydride are all charged to the reactor at once, filling the reactor to capacity. The reaction was then carried out under essentially the same conditions of pressure, temperature and time. A yield of 15,257 parts of polyester polyol having a hydroxyl number of 356 and an acid number of 1.8 was obtained. The amount of polyol represents a 3.6% decrease in yield over the process of the subject invention.

The embodiments of the invention in which an exclusive property or privilege is claimed are defined as follows:

1. In a process for the preparation of a polyester polyol by the esterification of a polycarboxylic acid or anhydride with a polyhydric alcohol the improvement which comprises:
   a. initially charging to a reactor an amount of a polycarboxylic acid or anhydride equal to between 3 to 16 weight percent in excess of stoichiometry;
   b. adding to the reactor a polyhydric alcohol and heating the charge to a temperature between 130° to 240° C.;
   c. removing from the reactor between 90 to 95 weight percent of the water of esterification resulting from step (b);
   d. charging to the reactor an amount of polyhydric alcohol substantially equivalent in weight to the amount of water of esterification removed from step (c); and
   e. continuing the esterification reaction until a polyol having an acid number of less than two is obtained.

2. The process of claim 1 wherein the polycarboxylic acid is adipic acid.

3. The process of claim 1 wherein the amount of polycarboxylic acid employed in the initial charge is equal to between 6 to 12 weight percent in excess of stoichiometry.

4. The process of claim 1 wherein the polyhydric alcohol is selected from the group consisting of ethylene glycol, diethylene glycol, 1,4-butane diol and mixtures thereof.

5. The process of claim 4 wherein the polyhydric alcohol is ethylene glycol.

6. The process of claim 1 wherein a catalyst is employed in step (e).

* * * * *